US010668182B2

(12) United States Patent
Ryu et al.

(10) Patent No.: US 10,668,182 B2
(45) Date of Patent: Jun. 2, 2020

(54) METHOD FOR PREPARING A MEDICAL MATERIAL FOR REPLACING A HARD TISSUE DEFECT AND A MEDICAL MATERIAL PREPARED THEREFROM

(71) Applicant: Bioalpha Corporation, Seoul (KR)

(72) Inventors: Mi Young Ryu, Gyeonggi-do (KR);
Sung Nam Park, Gyeonggi-do (KR);
Jun Hyuk Seo, Gyeonggi-do (KR);
Hyun Seung Ryu, Gyeonggi-do (KR)

(73) Assignee: Bioalpha Corporation, Seoul (KR)

( * ) Notice: Subject to any disclaimer, the term of this patent is extended or adjusted under 35 U.S.C. 154(b) by 0 days.

(21) Appl. No.: 15/754,104

(22) PCT Filed: Aug. 19, 2016

(86) PCT No.: PCT/KR2016/009199
§ 371 (c)(1),
(2) Date: Feb. 21, 2018

(87) PCT Pub. No.: WO2017/034243
PCT Pub. Date: Mar. 2, 2017

(65) Prior Publication Data
US 2018/0256779 A1    Sep. 13, 2018

(30) Foreign Application Priority Data
Aug. 21, 2015   (KR) .......................... 10-2015-0118166

(51) Int. Cl.
*A61L 27/10* (2006.01)
*A61L 27/44* (2006.01)
(52) U.S. Cl.
CPC ............. *A61L 27/10* (2013.01); *A61L 27/446* (2013.01); *A61L 2430/02* (2013.01); *A61L 2430/12* (2013.01); *A61L 2430/38* (2013.01)

(58) Field of Classification Search
CPC ............. A61L 2430/02; A61L 2430/12; A61L 2430/38; A61L 27/10; A61L 27/446
See application file for complete search history.

(56) References Cited

U.S. PATENT DOCUMENTS 5,125,971 A    6/1992   Nonami et al.
5,977,204 A *  11/1999  Boyan ...................... C08K 9/00
                                                523/113
(Continued)

FOREIGN PATENT DOCUMENTS

JP    S63318950 A    12/1988
JP    H07/232930      9/1995
(Continued)

OTHER PUBLICATIONS

Reyes et al. (Bioactive Glass-Ceramine Scaffolds with High-Strength for Orthopedic Applications 2014; pp. 1-10: in Ceramic Transactions • Sep. 2014 vol. 251). 15 total pages. (Year: 2014).*

(Continued)

*Primary Examiner* — Ernst V Arnold
(74) *Attorney, Agent, or Firm* — Cesari and McKenna, LLP

(57) ABSTRACT

The present invention relates to a method for preparing a medical material for replacing a hard tissue defect and a medical material produced therefrom. More specifically, in the present invention, powders of bioactive glass are press-molded, and are then subjected to a first heat treatment at a relatively low temperature below the glass transition temperature of bioactive glass. Then, the resultant is processed into a desired shape and then subjected to a second heat treatment at a temperature higher than the glass transition temperature of bioactive glass. Accordingly, the present invention provides a medical material which can be customized to a desired shape of a hard tissue defect in a living body and minimize thermal shock, and which is capable of (Continued)

exhibiting a bone fusion property, while overcoming the low compressive strength drawback of hydroxyapatite, which is an existing hard tissue replacement material currently in use.

10 Claims, 5 Drawing Sheets

(56) References Cited

U.S. PATENT DOCUMENTS

| | | |
|---|---|---|
| 7,332,452 B2 | 2/2008 | Ogawa et al. |
| 2005/0011227 A1* | 1/2005 | Sakai .................. C03B 11/122 65/29.21 |
| 2008/0038534 A1 | 2/2008 | Zenati et al. |

FOREIGN PATENT DOCUMENTS

| | | |
|---|---|---|
| KR | 2007/0039609 A | 4/2007 |
| KR | 2009/0077650 A | 7/2009 |
| KR | 2012/0083675 A | 7/2012 |
| WO | WO-2011/130812 A2 | 10/2011 |

OTHER PUBLICATIONS

Reyes et al. (Structural Characterization and Mechanical Evaluation of Bioactive Glass 45S5 Foams Obtained by a Powder Technology Approach Journal of the American Ceramic Society • Dec. 2012;95(12):3776-3780) 6 pages total. (Year: 2012).*

* cited by examiner

[Fig. 1]
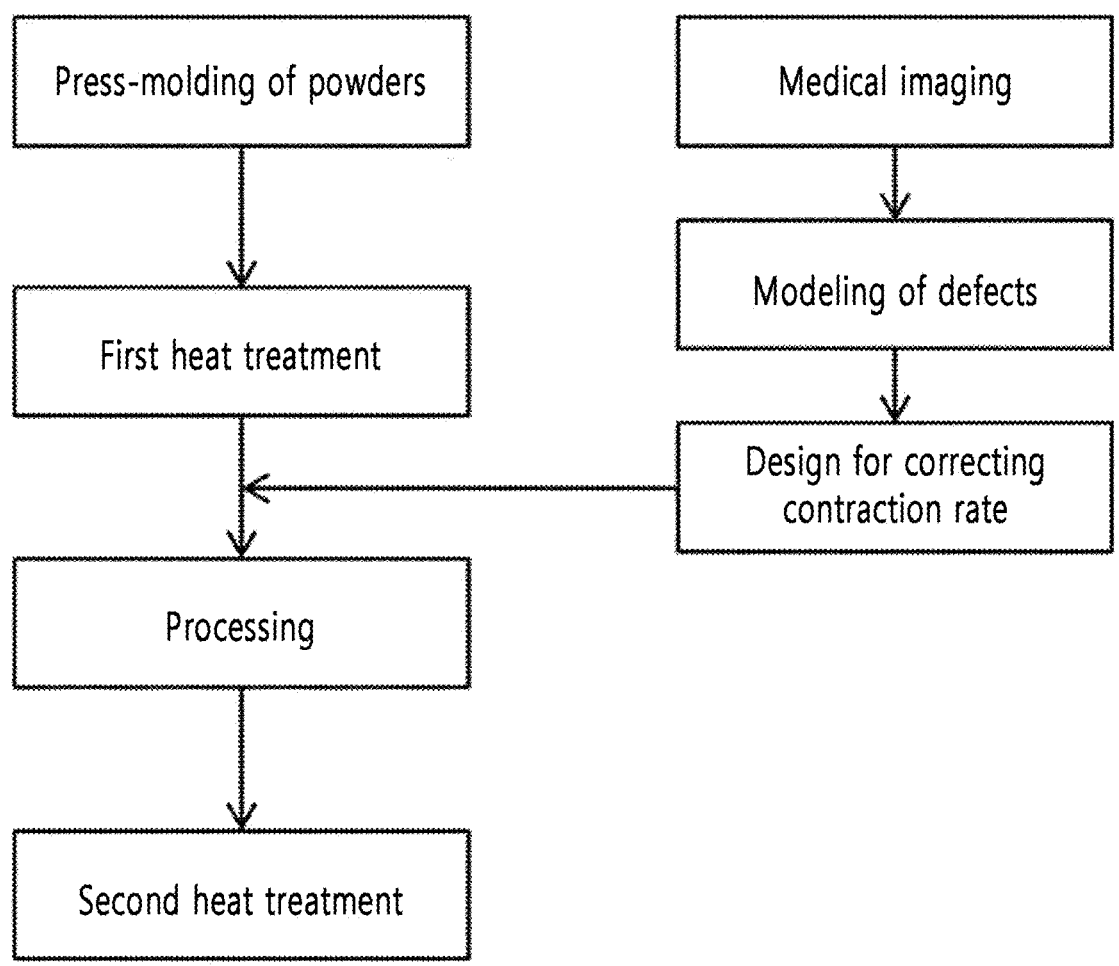

[Fig. 2]
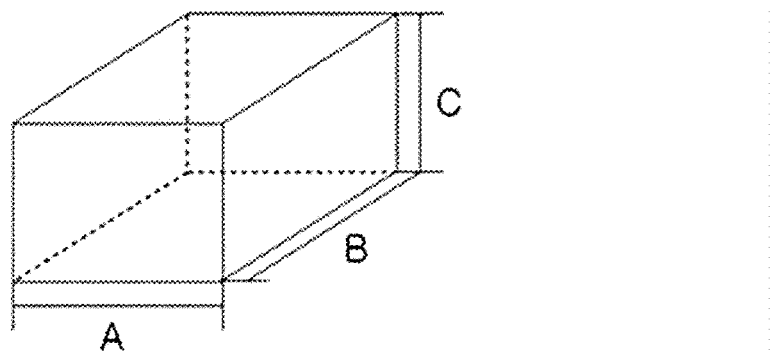
| First heat treatment | A axis (%) | B axis (%) | C axis (%) |
|---|---|---|---|
| 700°C | 1.86±0.19 | 1.98±0.28 | 1.86±0.22 |
| 750°C | 16.95±0.22 | 17.41±0.05 | 16.89±0.37 |
[Fig. 3]
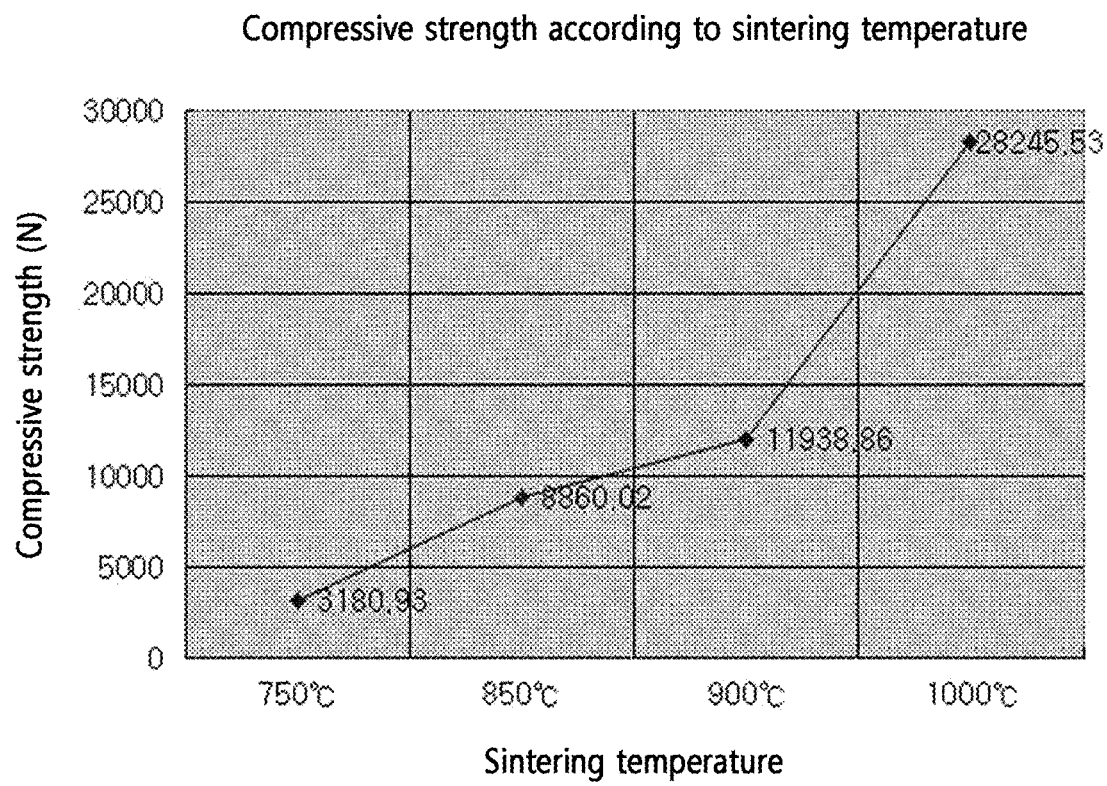

[Fig. 4]
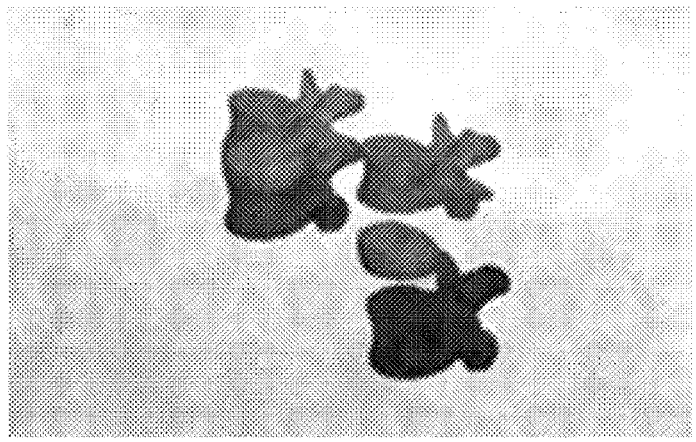
[Modeling product of spine model]
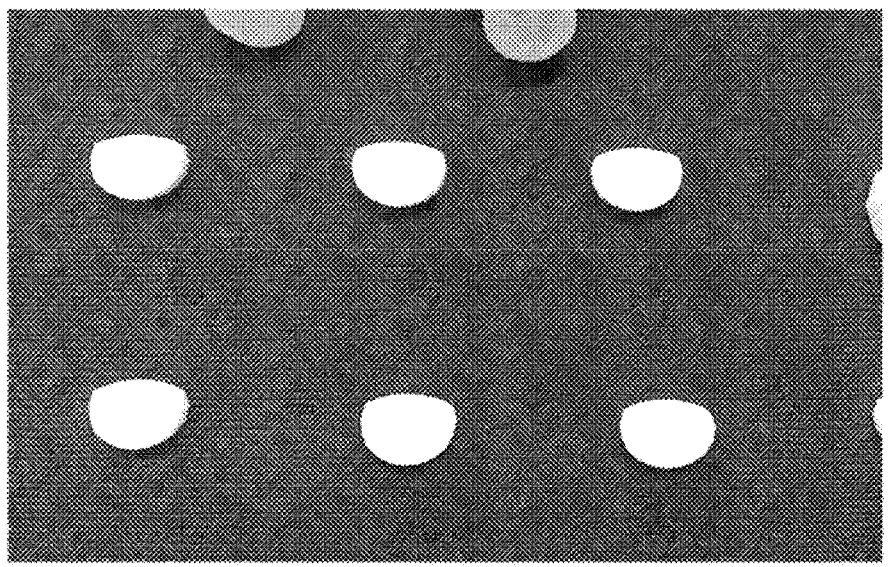
[Disk-shaped customized product]

[Fig. 5]
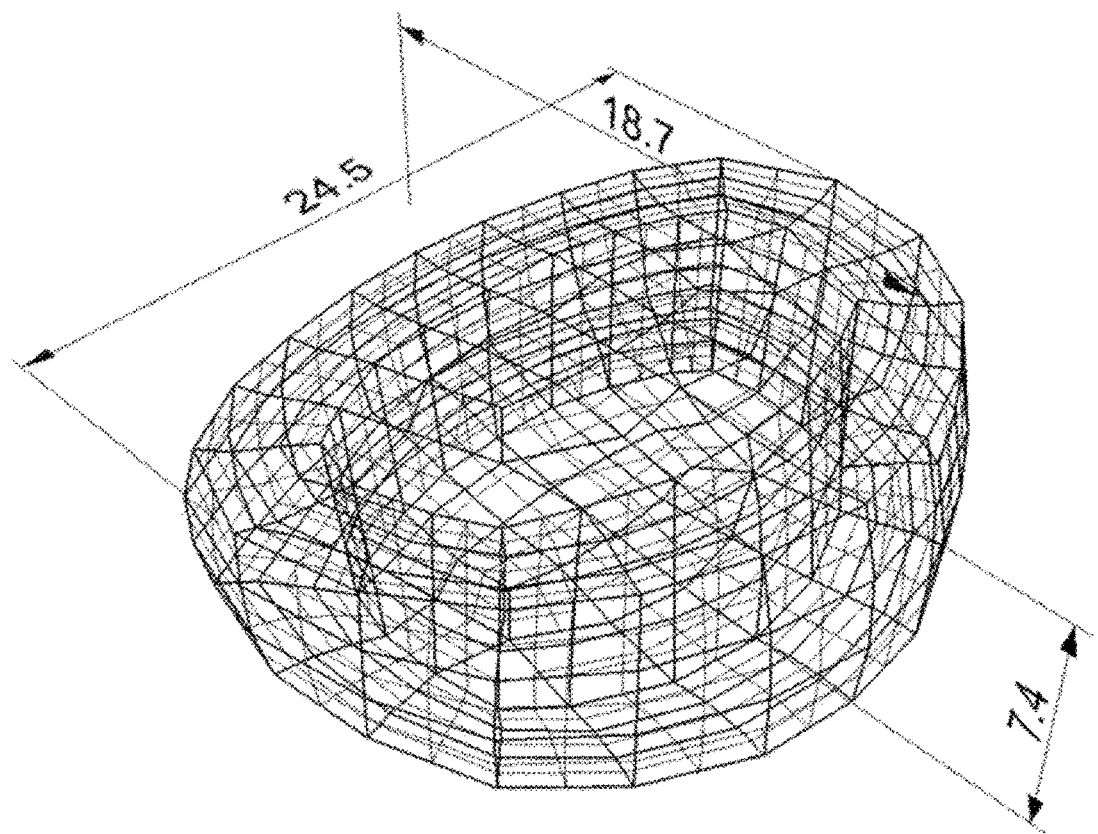
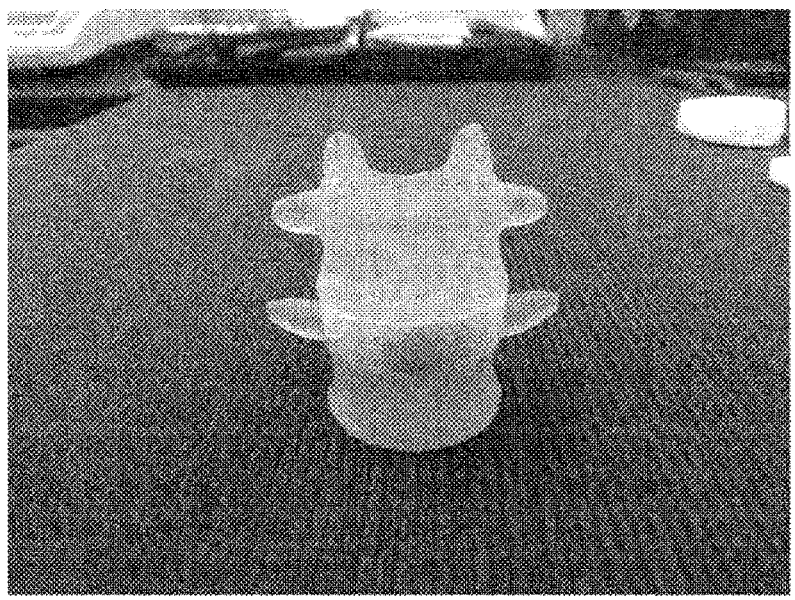

[Fig. 6]
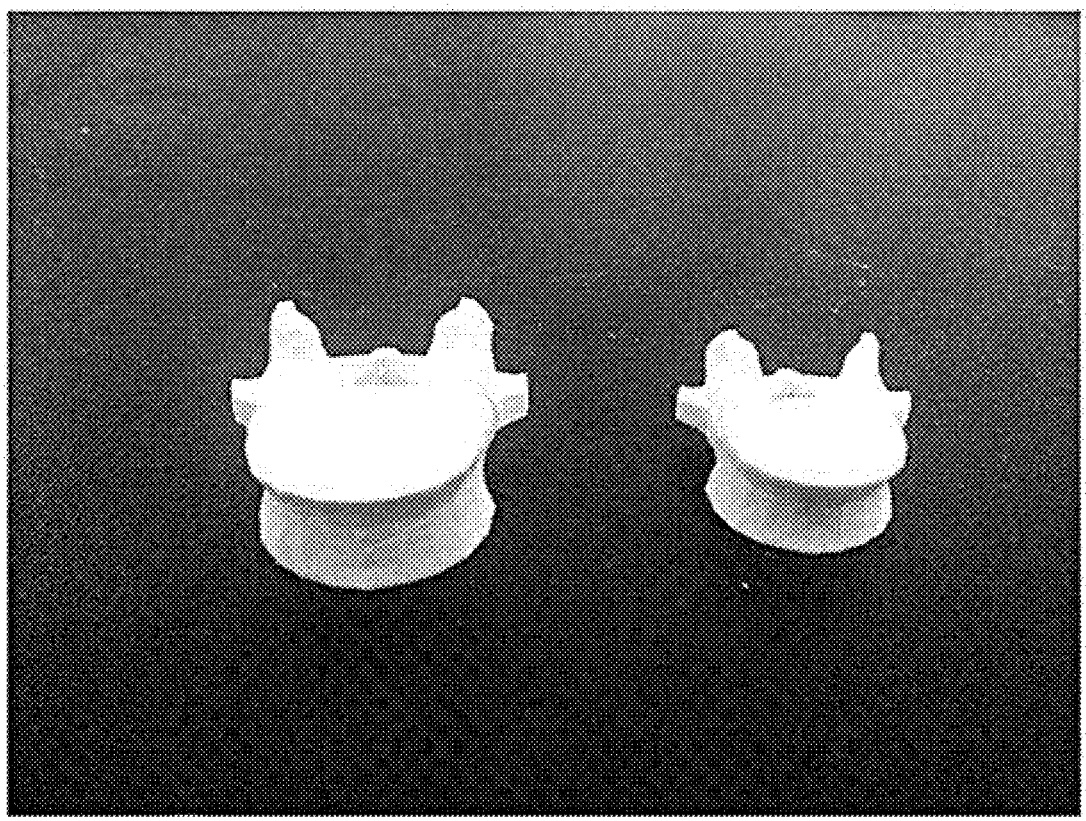
[Molded product after first heat treatment followed by processing (Left) and Final product after second heat treatment (Righy)]
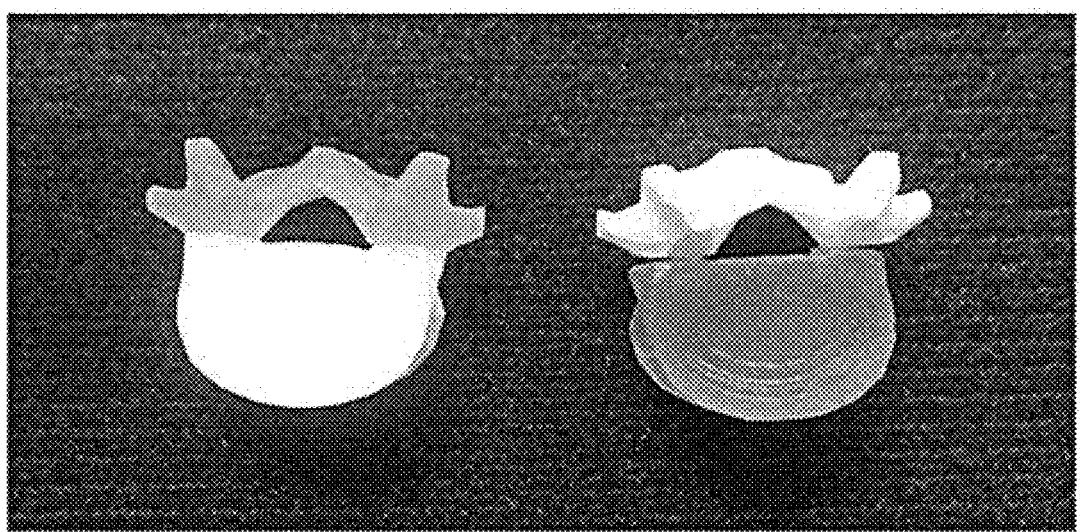
[Images of pairing final sintered product with 3D-printed molded product]

METHOD FOR PREPARING A MEDICAL MATERIAL FOR REPLACING A HARD TISSUE DEFECT AND A MEDICAL MATERIAL PREPARED THEREFROM

CROSS-REFERENCE TO RELATED APPLICATIONS

This application is the National Stage of International Application No. PCT/KR2016/009199, filed Aug. 19, 2016, which claims the benefit of Korean Application No. 10-2015-0118166, filed on Aug. 21, 2015. The contents of both applications are hereby incorporated by reference in their entirety.

TECHNICAL FIELD

The present invention relates to a method for preparing a medical material for replacing a hard tissue defect and a medical material prepared therefrom.

BACKGROUND ART

Hard tissues constituting the human body are composed of 67 wt % inorganic material and 33 wt % organic material, and the inorganic material is composed of apatite, the major ingredient of which is Ca/P. Since the composition ratio of inorganic material is high, substitution is possible by using synthetic hydroxyapatite when a hard tissue defect occurs. However, synthetic hydroxyapatite has a disadvantage in that it is difficult to apply to various sites requiring mechanical stability due to its low compressive strength.

Hydroxyapatite is a representative osteoconductive material which directly attaches to bone when it makes its contact with a peripheral defect in graft sites. The material causes bone fusion when it is in exact contact with a defect site. However, if the material is not in contact with the defect site, it may damage surrounding bones by micro-motion of a graft material. Accordingly, the design thereof can be tailored exactly to the graft site in order to enhance a therapeutic effect.

The characteristics of typical ceramic materials are excellent in compressive strength, hardness, and abrasion resistance. Further, since ceramic materials exist in the form of oxides, they have excellent resistance to corrosion caused by chemical substances. The excellent physical/chemical stability of ceramic materials has the advantage of significantly increasing life expectancy when used in various parts. However, due to the rigidity of the materials, processing thereof is difficult, and as a result, the preparation of a complex molded product is not possible.

Since the rigidity of ceramic materials appears due to heat treatment, e.g., sintering, it is common to complete the molding before the heat treatment, and after the heat treatment, some of the materials are processed using a polishing method. Ceramic molded products can be produced by simply applying pressures to powders before sintering, or by making the powder into a slurry state and then casting, injection molding, or extrusion molding the same. The molded products produced as above are treated with heat at the sintering temperature of raw materials, and the preparation is thereby completed. When molding a product design before heat treatment, a mold implementing the same is required, and the mold can only be used for production of the corresponding design.

When various designs of products are implemented, it is necessary to apply the processing after heat treatment. Due to the characteristics of ceramics, such method is disadvantageous in that it requires considerable time and costs. In addition, as the high hardness of the surface is likely to cause defects during impractical processing, a defect rate may be increased due to the processing. If damage occurs due to a processing defect after grafting the same into a human body, not only is the graft site severely damaged, but also re-operation should be carried out.

Therefore, when preparing a material for replacing a hard tissue, it is essential to produce a material which is tailored to fit the defect site exactly.

DISCLOSURE

Technical Problem

An object of the present invention is to provide a tailored medical material for replacing a hard tissue defect that fits a defect site exactly and a method for preparing the same.

Technical Solution

A first aspect of the present invention provides a medical material for replacing a hard tissue defect in a living body, comprising: a first step of preparing a molded product by press-molding powders of bioactive glass; a second step of subjecting the molded product to a first heat treatment at 650° C. to 745° C.; a third step of processing the heat-treated molded product to form a shape of a hard tissue defect, said shape being adapted according to a predetermined contraction rate during a second heat treatment; and a fourth step of subjecting the processed product to a second heat treatment at 850° C. to 1,200° C.

A second aspect of the present invention provides a medical material for replacing a hard tissue defect in a living body, which is prepared by the method of the first aspect and is thereby prepared within an error range of 5% or less based on a length in a single-axis direction of a form of the hard tissue defect.

Advantageous Effects

Throughout the present invention, embodying a complicated form of a high-strength bioactive glass material is possible, and accordingly, a medical material tailor-made for a hard tissue defect of a patient can be provided. When the preparation method according to the present invention is applied, since the material retains the high-strength properties of a conventional bioactive crystallized glass, the material can be used not only for general structures of hard tissues but also for defects in the spine or facial area where mechanical stability is required.

BRIEF DESCRIPTION OF THE DRAWINGS

FIG. 1 is a mimetic diagram of a method for preparing the medical material according to the present invention for replacing a hard tissue defect in a living body.

FIG. 2 shows the investigation result of the contraction rate in each axis according to temperatures in the first heat treatment.

FIG. 3 shows the investigation result of the compressive strength of the molded product according to temperatures in the second heat treatment.

FIG. 4 shows a modeling product of the spine model and the disc-shaped tailored product prepared according to an embodiment of the present invention by using the same.

FIG. 5 shows the images of pairing the disc sintered product, which were tailored, with the peripheral spine model.

FIG. 6 shows the images of the spine-shaped molded product after the first heat treatment followed by processing (top left) and the final product after the second heat treatment (top right), which were prepared according to an embodiment of the present invention, and shows the mages of pairing the final sintered product with a 3D-printed molded product.

BEST MODE

A first aspect of the present invention provides a method for preparing a medical material for replacing a hard tissue defect in a living body, comprising: a first step of preparing a molded product by press-molding powders of bioactive glass; a second step of subjecting the molded product to a first heat treatment at 650° C. to 745° C.; a third step of processing the heat-treated molded product to form a shape of a hard tissue defect, said shape being adapted according to a predetermined contraction rate during a second heat treatment; and a fourth step of subjecting the processed product to a second heat treatment at 850° C. to 1,200° C.

A second aspect of the present invention provides a medical material for replacing a hard tissue defect in a living body, which is prepared by the method according to the first aspect and is thereby prepared within an error range of 5% or less based on a length in a single-axis direction of a form of the hard tissue defect.

Hereinbelow, the constitution of the present invention will be described in detail.

Hydroxyapatite has mainly been used as an existing medical material for replacing a hard tissue defect. However, hydroxyapatite has a disadvantage in that it is difficult to apply to various sites requiring mechanical stability due to its low compressive strength.

On the other hand, bioactive glass is a biocompatible material exhibiting a bone fusion characteristic, in which the glass is directly attached to bone, and therefore, it has been used as a biomaterial for bone repair and generation by injection into a living body mainly as a paste. When the bioactive glass is calcined at a high temperature, it is transformed into a crystalline state, and can thus exhibit a high compressive strength. However, once the bioactive glass is transformed into the crystalline state, it is difficult to be freely processed into a desired form matched to the shape of an in vivo hard tissue defect due to its high compressive strength. As a result, the bioactive glass has a disadvantage in that the processing time and costs are increased. In addition, because the bioactive glass is liquefied by passing the glass transition temperature ($T_g$), breakage due to thermal shock may occur.

In the present invention, powders of bioactive glass were press-molded, and then subjected to a first heat treatment at a relatively low temperature, i.e. below the glass transition temperature of the bioactive glass. Then, the resultant was processed into a desired form, and then subjected to a second heat treatment at a temperature higher than the glass transition temperature of the bioactive glass. Accordingly, it was discovered that a medical material can be produced which can be tailored to a desired form which is matched to the shape of a hard tissue defect in a living body via the preparation method mentioned above while minimizing thermal shock, and which is capable of exhibiting a bone fusion property, while overcoming the low compressive strength drawback of hydroxyapatite, which is an existing hard tissue replacement material currently in use. Additionally, in the present invention, the molded product was uniformly and isotropically contracted during the heat treatment by controlling the first and second heat treatment conditions for the press-molded product of the bioactive glass powders. Therefore, it was found that the finally produced medical material for replacing a hard tissue defect can be produced and tailored within an error range of 5% or below based on the length in a single-axis direction of the shape of a hard tissue defect in vivo. As described above, the medical material of the present invention for replacing a hard tissue defect is composed of high-strength bioactive crystallized glasses adhered directly to a bone, and therefore, the material can be applied to a site requiring mechanical stability. The present invention is based on these findings.

That is, the present invention is characterized in that in order to tailor-make a bioactive crystallized glass through heat treatments of bioactive glass, the first heat treatment was carried out at a relatively low temperature such that a product can be easily processed with a general processing device, and then a final product is produced by subjecting the thus-processed molded product to the second heat treatment.

As shown in FIG. 1, the method of the present invention for preparing a medical material for replacing a hard tissue defect in a living body comprises a first step of preparing a molded product by press-molding powders of bioactive glass;

a second step of subjecting the molded product to a first heat treatment at 650° C. to 745° C.;

a third step of processing the heat-treated molded product to form a shape of a hard tissue defect, said shape being adapted according to a predetermined contraction rate during a second heat treatment; and a fourth step of subjecting the processed product to a second heat treatment at 850° C. to 1,200° C.

Preferably, the method of the present invention may further comprise a fifth step of performing a slow cooling of the processed product subjected to the second heat treatment after the fourth step.

The first step is a step of preparing a molded product by press-molding bioactive glass in a powder state.

As used herein, the term "bioactive glass" refers to a glass component that exhibits bioactivity because hydroxyapatite is formed on the surface when it is grafted into living tissues; that is, the term generally refers to a glass composed of inorganic materials.

The bioactive glass is not particularly limited in the present invention, and any glass known in the art can be used. Representatively, a $SiO_2$—CaO-based bioactive glass, i.e., bioactive glass containing calcium oxide (CaO) and silicon oxide ($SiO_2$) as main ingredients, can be used. In the present invention, the bioactive glass may further contain at least one of MgO, $B_2O_3$, $P_2O_5$, and $CaF_2$.

Specifically, the bioactive glass can be subjected to various changes in a basic composition of the bioactive glass, which is approved by the Food and Drug Administration (FDA) and commercially available under the trademark of Bioglass™. The Bioglass™ composition is known as 45S5. In an embodiment of the present invention, the bioactive glass may include 40 mol % to 70 mol % of $SiO_2$ and 30 mol % to 60 mol % of CaO. In another embodiment of the present invention, the bioactive glass may include 35 mol % to 65 mol % of $SiO_2$, 10 mol % to 50 mol % of CaO, and 1 mol % to 40 mol % of at least one selected from MgO, $B_2O_3$, $P_2O_5$, and $CaF_2$. Examples of various compositions of the bioactive glass are as follows:

45S5: 46.1 mol % $SiO_2$, 26.9 mol % CaO, 24.4 mol % $Na_2O$, and 2.5 mol % $P_2O_5$.

58S: 60 mol % $SiO_2$, 36 mol % CaO, and 4 mol % $P_2O_5$.

70S30C: 70 mol % $SiO_2$, and 30 mol % CaO.

S53P4: 53 mol % $SiO_2$, 23 mol % $Na_2O$, 20 mol % CaO, and 4 mol % $P_2O_5$.

In the present invention, the average particle size of the bioactive glass powder may be 0.5 µm to 5 µm. Specifically, the average particle size of the bioactive glass powder suitable for molding in the present invention is 1.8 µm and is limited to a maximum value of 5 µm.

In the present invention, the bioactive glass powders in the molded product can be uniformly distributed by further mixing the bioactive glass powders with a dispersant and then press-molding the same. Examples of the dispersant may be at least one kind of polyvinyl alcohol (PVA), polyvinyl butyral (PVB), poly(methyl methacrylate) (PMMA), polyethylene glycol (PEG), methylcellulose, hydroxy methylcellulose, sodium carboxymethyl cellulose, paraffin, wax emulsion, microcrystalline wax, ethanol, etc.

The press-molding in the first step may be cold isostatic pressing (CIP).

The molded body obtained from the first step may have various forms such as a block form, a cylindrical form, etc.

In the second step, the molded product obtained from the first step is subjected to the first heat treatment at 650° C. to 745° C., thereby condensing it to a strength level that enables processing of the molded product.

The first heat treatment should be able to achieve a level of strength that is capable of processing the molded product of the bioactive glass. When the temperature is below 650° C., the condensation of the molded product does not proceed, and thus the molded product can be easily damaged after processing. When the heat treatment is carried out at a temperature of 750° C. or higher, the strength and hardness of the molded product increase because the molded product rapidly contracts, and thereby processing is not possible. In the present invention, it was confirmed that when the first heat treatment was carried out at 750° C. and then the second heat treatment was carried out thereafter, severe damage in the molded product occurred. Therefore, in the present invention, the temperature range of the first heat treatment was set to 650° C. to 745° C. Among these, the most suitable temperature may be 700° C. When the first heat treatment was carried out at 700° C., the volume of the molded product contracted by approximately 5%, and the linear contraction rate, e.g., the contraction rate based on the length in a single-axis direction was approximately 2% (FIG. 2).

The third step is a step of processing the molded product, which was subjected to the first heat treatment in the second step, to a shape of a hard tissue defect in consideration of the contraction rate during the second heat treatment.

For the processing in the third step, a medical image may first be obtained and defect modeling may be carried out based on the medical image. Thereafter, the contraction rate during the second heat treatment is applied to the defect modeling result in order to re-model the defect, and then the molded product subjected to the first heat treatment is processed based on the above defect re-modeling result.

The processing of the molded body subjected to the first heat treatment may be carried out using a method, apparatus, and/or device commonly used for processing a medical material for replacing a hard tissue defect in a living body. Specifically, the processing may be carried out using a CNC milling machine capable of multi-axis processing, or a 5-axis processing machine, a dental prosthesis processing machine, etc.

In the fourth step, the processed product obtained from the third step is subjected to the second heat treatment at 850° C. to 1,200° C. for sintering, thereby forming a high-strength bioactive crystallized glass.

In the present invention, as described above, the contraction during the second heat treatment can be controlled by isotropic contraction through adjustment of a heat treatment condition by carrying out the second heat treatment at 850° C. to 1,200° C. following processing after the first heat treatment at 650° C. to 750° C. That is, the contraction rate during the second heat treatment in the fourth step, by which the shape (including dimensions) of the medical material is finally determined, can be controlled occurring constant within an error range of 5% or less based on each length in an axial direction through the heat treatment conditions according to the present invention.

In the present invention, the contraction rate during the second heat treatment may be 15% to 25%, for example, 16% to 20%, or 17% to 19% based on the length in a single-axis direction. In the present invention, the contraction rate of the volume during the second heat treatment may be 30% to 55%, for example, 40% to 50%.

In the present invention, as described above, the bioactive glass contains $SiO_2$ as a main ingredient, and thereby its glass transition temperature ($T_g$) does not deviate greatly from 800° C. In the present invention, the $T_g$ was excluded from the heat treatment temperature as severe damage occurred in the bioactive glass processed product at such glass transition temperature, 800° C., regardless of sintering conditions.

In the present invention, compressive strength after sintering at a temperature of 700° C. or higher was evaluated in order to confirm a suitable temperature in the second heat treatment. Compressive strength of 3,000 N or higher was observed from 750° C., a sintering temperature causing rapid contraction of the product. Additionally, as a sintering temperature increased, the compressive strength was greatly increased. In particular, it was confirmed that when the second heat treatment was carried out at 1,000° C., compressive strength was 25,000 N or higher, indicating that mechanical properties of a high-strength bioactive crystallized glass were exhibited (FIG. 3). Therefore, it was confirmed that the first heat treatment, processing, and second heat treatment according to the present invention maintained an inherent property of the bioactive glass, and that the optimal temperatures during the first and second heat treatments for achieving the same were 700° C. and 1,000° C., respectively.

The fifth step is a step of finally obtaining a medical material for replacing a hard tissue defect in a living body by slowly cooling the processed product subjected to the second heat treatment.

During the second heat treatment of the bioactive crystallized glass subjected to the first heat treatment, the bioactive crystallized glass rapidly contracts as it passes through $T_g$ of the material, and then condenses. Due to the properties of glass materials, liquid phase sintering proceeds while passing through $T_g$, and severe damage is generated if thermal shock occurs within the corresponding temperature range. Therefore, after the second heat treatment (sintering), the temperature should be gradually lowered to slowly cool a molded product such that there is no thermal shock. If the slow-cooling rate after the second heat treatment is 5° C./min, severe damage in the molded product occurs, and therefore, the slow-cooling rate should be less than 5° C./min. Accordingly, the slow-cooling rate in the fifth step may be controlled to be less than 5° C./min. Specifically, it was confirmed in the present invention that damage did not occur in a sintered product during the slow cooling at 2° C./min.

In the present invention, it is possible to provide a medical material for replacing a hard tissue defect in a living body, which is prepared with an error range of 5% or less based on a length in a single-axis direction of a shape of a hard tissue defect in a living body, using the methods described above.

The medical material according to the present invention for replacing a hard tissue defect in a living body may exhibit compressive strength of 8,000 N or higher, for example, 25,000 N or higher, specifically 8,000 N to 35,000 N.

The medical material according to the present invention for replacing a hard tissue defect in a living body may exhibit a bone fusion property as an inherent property of bioactive glass, and thereby the material can effectively replace a hard tissue defect in a living body when grafted in vivo.

Specifically, the medical material according to the present invention may be an artificial bone, an artificial joint, an oral maxillofacial bone and a cranial bone for orthopedic use, or an artificial dental implant for dental use. For example, the medical material according to the present invention may be a disc-shaped artificial bone capable of being used in spinal fusion surgery, or an artificial bone used for facial reconstruction surgery.

[Mode of the Invention]

Hereinbelow, the present invention will be described in detail with accompanying exemplary embodiments. However, the exemplary embodiments disclosed herein are only for illustrative purposes and should not be construed as limiting the scope of the present invention.

EXAMPLE 1

Investigation of Contraction Rate Depending on Temperature for First Heat Treatment Bioactive glass powders (average diameter of particles: 1.8 μm), which are composed of 46.1 mol % $SiO_2$, 26.9 mol % CaO, 24.4 mol % $Na_2O$, and 2.5 mol % $P_2O_5$, were isostatically pressed using cold isostatic pressing (CIP) to prepare a block-shaped molded product.

The thus-prepared molded product was subjected to first heat treatments at 600° C., 700° C., and 750° C. Then, the contraction rate in each axis depending on each temperature of the first heat treatment was investigated.

The results of the first heat treatments at 700° C. and 750° C. were representatively shown in FIG. 2.

First, at 600° C., which is a temperature below 650° C., condensation of a molded product did not progress, and thus it was shown that the molded product was easily damaged after processing the same.

It was confirmed from FIG. 2 that when the heat treatment was carried out at 750° C., the molded product of the bioactive crystallized glass rapidly contracted, and as a result, processing was not possible because the strength and hardness of the molded product were increased. On the contrary, it was confirmed that when the heat treatment was carried out at 700° C., the volume of the molded product contracted by approximately 5% and the linear contraction rate was 2%.

EXAMPLE 2

Establishment of Temperature Condition in Second Heat Treatment and Investigation of Contraction Rate Depending on Temperature for Second Heat Treatment The block-shaped molded product prepared in Example 1 was subjected to the first heat treatment at 700° C., and then sintered at a temperature of 700° C. or higher in order to confirm a suitable temperature for a second heat treatment. Thereafter, the compressive strength was evaluated.

The results are shown in FIG. 3.

It was confirmed in FIG. 3 that the compressive strength of 3,000 N or higher was observed from 750° C., a temperature exhibiting rapid contraction, and that as a sintering temperature increased, the compressive strength was greatly increased. In particular, it was confirmed that when the second heat treatment was carried out at 1,000° C., compressive strength was 25,000 N or higher, indicating that the mechanical properties of a conventional high-strength bioactive crystallized glass were maintained. Therefore, it was confirmed that the preparation method composed of the first heat treatment, processing, and second heat treatment in order, suggested in the present invention, helped an inherent property of the bioactive glass maintained, and that the optimal temperatures during the first and second heat treatments for achieving the same were 700° C. and 1,000° C., respectively.

The contraction rate in each axis was investigated when the first heat treatment was carried out at its optimal temperature (700° C.), followed by carrying out the second heat treatment at its optimal temperature (1,000° C.); these optimal temperatures were confirmed above.

The results are shown in Table 1 below.

TABLE 1

| Contraction rate after second heat treatment | A-axis (%) | B-axis (%) | C-axis (%) | Volume (%) |
| --- | --- | --- | --- | --- |
| 1,000° C. | 18.64 ± 0.89 | 18.47 ± 0.15 | 17.97 ± 0.2 | 45.58 ± 0.77 |

It was confirmed from Table 1 that when the first heat treatment was carried out at 700° C., followed by the second heat treatment at 1,000° C., the molded product had uniformly contracted in width, length, and height directions, thereby showing a contraction rate of about 18%. The volume of the final molded product after the second heat treatment was contracted by 45% compared to that subjected to the first heat treatment.

EXAMPLE 3

Preparation of a Disc-Shaped Medical Material Using the Method of the Present Invention In the case of preparing a tailored product by using a first heat treatment, processing, and a second heat treatment for a bioactive crystallized glass, i.e., a molded product of bioactive glass powders, design of the tailored product must be made by applying a contraction rate at each axis.

In the Example, as confirmed in Example 2, a contraction rate of 18% in each axis was applied, and a disc-shaped medical material capable of being used for spinal fusion was produced. As a result, it was confirmed that the medical material was produced in the same manner as the predicted design.

Specifically, the block-shaped molded product prepared in Example 1 was subjected to the first heat treatment at 700° C. to obtain a molded product. Then, as shown in FIG. 4, the results of the spinal- and disc-shaped models were analyzed, and then the disc-shape was extracted. Thereafter, the contraction rate of 18% was applied to each axis of the corresponding design for re-design. The molded product subjected to the first heat treatment was processed. The disc-shaped sintered product (FIG. 4), which was obtained by being subjected to the second heat treatment at 1,000° C. followed by slowly cooling at 2° C./min, showed a deviation of less than 5% from the predicted design (Table 2). In addition, it was confirmed that the size and curvature were exactly matched when the upper and lower parts of the vertebral body were paired with those of the 3D-printed model, indicating that tailored preparation thereof was possible.

TABLE 2

| Classification | A (mm) | B (mm) | C (mm) |
| --- | --- | --- | --- |
| Design | 24.5 | 18.7 | 7.4 |
| Actual measurement value | 24.46 ± 0.13 | 18.53 ± 0.15 | 7.57 ± 0.49 |
| Error | 0.16% | 0.9% | 2.3% |

EXAMPLE 4

Preparation of a Medical Material in the Shape of a Spine Using the Method of the Present Invention It was confirmed that when the medical material was produced using the method of the present invention described in Example 3, a complicated spine form in addition to the disc-shape could be effectively achieved.

Specifically, the block-shaped molded product prepared in Example 1 was subjected to the first heat treatment at 700° C. to obtain a molded product. Then, as shown in FIG. 5, when the molded product processed by tailoring the same with the spine-shaped design was compared to the product after the second heat treatment, it was confirmed that the molded product had uniformly contracted in an isotropic manner (FIG. 6). In addition, it was confirmed that when molded product in the shape of a part of spine was paired with 3D-printed prototype in the shape of another part, the overall spinal shape perfectly was established, indicating that the preparation process thereof has a superior effect in achieving the shape (FIG. 6).

The invention claimed is:

1. A method for preparing a medical material for replacing a hard tissue defect in a living body, comprising:
    a first step of preparing a molded product by press-molding powders of bioactive glass;
    a second step of subjecting the molded product to a first heat treatment at 650° C. to 745° C.;
    a third step of designing a product shape based on a predetermined contraction rate during a second heat treatment, the product shape having the shape of a hard tissue defect within an error range of 0-5% based on a length in a single-axis direction of the shape of the hard tissue defect, and machining the first heat-treated product to form the designed product shape; and
    a fourth step of subjecting the machined product to a second heat treatment at 850° C. to 1,200° C.
wherein the bioactive glass comprises CaO, $SiO_2$, $Na_2O$, and $P_2O_5$.

2. The method according to claim 1, further comprising a fifth step of performing a slow cooling of the machined product subjected to the second heat treatment after the fourth step.

3. The method according to claim 1, wherein the bioactive glass further comprises at least one selected from MgO, $B_2O_3$, and $CaF_2$.

4. The method according to claim 1, wherein the powders of the bioactive glass are further mixed with a dispersant, followed by press-molding.

5. The method according to claim 4, wherein the dispersant is polyvinyl alcohol (PVA), polyvinyl butyral (PVB), poly(methyl methacrylate) (PMMA), polyethylene glycol (PEG), methylcellulose, hydroxy methylcellulose, sodium carboxymethyl cellulose, paraffin, wax emulsion, microcrystalline wax, ethanol, or a mixture thereof.

6. The method according to claim 1, wherein the press-molding in the first step is cold isostatic pressing (CIP).

7. The method according to claim 1, wherein the contraction during the second heat treatment is isostatic contraction.

8. The method according to claim 1, wherein the contraction rate during the second heat treatment is 15% to 25% based on the length in a single-axis direction.

9. The method according to claim 2, wherein the slow cooling in the fifth step is performed at a rate of less than 5° C./min.

10. The method according to claim 1, wherein the product shape in the third step is designed following the procedure shown below:
    obtaining a medical image of the living body,
    modeling the hard tissue defect based on the medical image, and
    re-modeling the modeled hard tissue defect by applying the predetermined contraction rate during the second heat treatment, thereby obtaining the product shape.

* * * * *